United States Patent [19]
Lee

[11] Patent Number: 4,676,780
[45] Date of Patent: Jun. 30, 1987

[54] SURGICAL APPARATUS FOR PERFORMING SUCTION LIPECTOMY

[76] Inventor: Hans Lee, Suite 200, 415 Morris St., Charleston, W. Va. 25301

[21] Appl. No.: 831,799

[22] Filed: Feb. 21, 1986

[63] Continuation-in-part of Ser. No. 887,040, filed as PCTUS85/000,814, May 6, 1985, published as WO85/05024 on Nov. 21, 1985, which is a continuation-in-part of Ser. No. 651,720, filed Sep. 18, 1984, Pat. No. 4,627,834, which is a a continuation-in-part of Ser. No. 607,714 filed May 17, 1984, Pat. No. 4,596,553.

[51] Int. Cl.$^4$ ............................................. A61M 5/00
[52] U.S. Cl. ................................... 604/117; 604/902; 604/49
[58] Field of Search .................. 604/902, 117, 49, 93, 604/35, 73, 49, 115; 33/42, 511, 512

[56] References Cited
U.S. PATENT DOCUMENTS

| | | | |
|---|---|---|---|
| 390,177 | 9/1888 | Lee | 604/280 |
| 504,352 | 9/1893 | Heysinger | 30/286 |
| 1,749,919 | 3/1930 | Mierley | |
| 2,198,666 | 4/1940 | Gruskin | 128/215 |
| 2,338,800 | 1/1944 | Burke | 128/315 |
| 2,545,115 | 3/1951 | Son | 128/215 |
| 2,559,474 | 7/1951 | Son | 604/117 |
| 2,705,949 | 4/1955 | Silverman | 128/2 |
| 2,715,899 | 8/1955 | MacLean | 128/2 |
| 2,876,539 | 3/1959 | Ford | 30/283 |
| 3,920,001 | 11/1975 | Edwards | 128/2 F |
| 4,235,234 | 11/1980 | Whitney et al. | 128/216 |
| 4,318,414 | 3/1982 | Schuster et al. | 128/759 |
| 4,536,180 | 8/1985 | Johnson | 604/268 |

Primary Examiner—Stephen C. Pellegrino
Assistant Examiner—J. L. Kruter
Attorney, Agent, or Firm—Lowe, Price, LeBlanc, Becker & Shur

[57] ABSTRACT

A cannula is provided with a guide bar, a rear end of which is formed with a mounting sleeve through which the cannula handle is clamped to the guide bar. The forward end of the guide bar carries a height adjustment bar having a pair of guide wheels rotatably mounted to a lower surface thereof between the guide bar and cannula tip. The height adjustment bar is provided with an elongate slot through which two screws pass for threaded connection to the forward end. Loosening of the screws permits the height adjustment bar to slide to vary the spacing between the guide wheels and cannula tip. The peripheral surface of each guide wheel is formed with an inner beveled edge that stretches the skin between the guide wheels during the suction lipectomy procedure enabling the cannula tip to travel at constant depth through the fatty tissue as the cannula is manually directed by the surgeon in reciprocating strokes.

13 Claims, 10 Drawing Figures

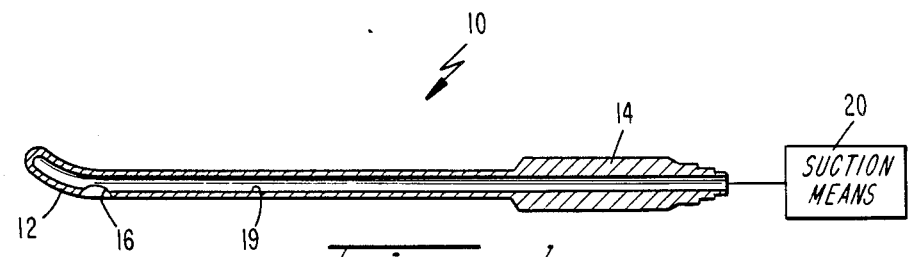
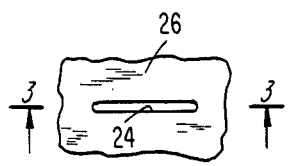
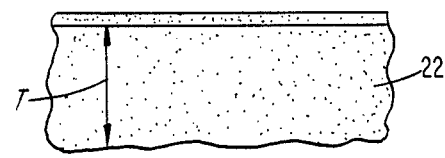
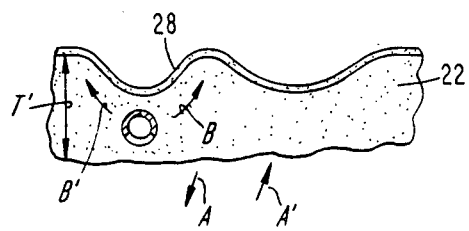
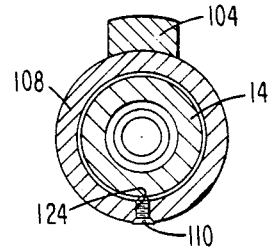
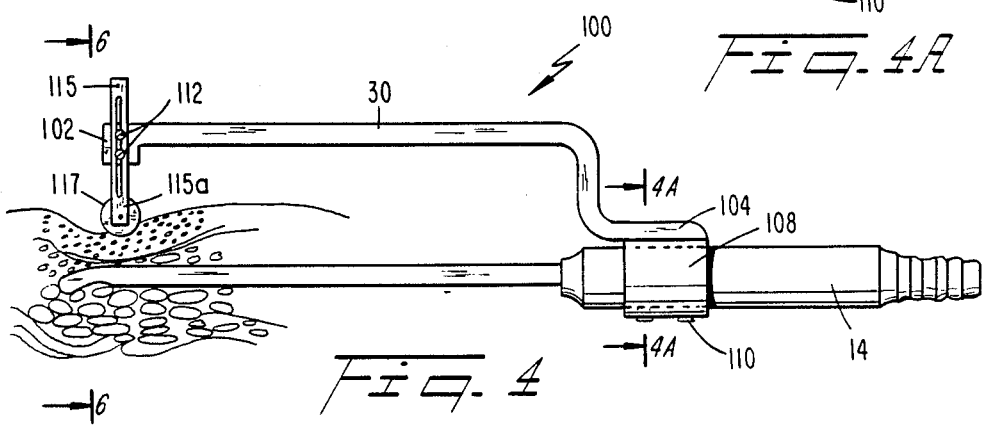

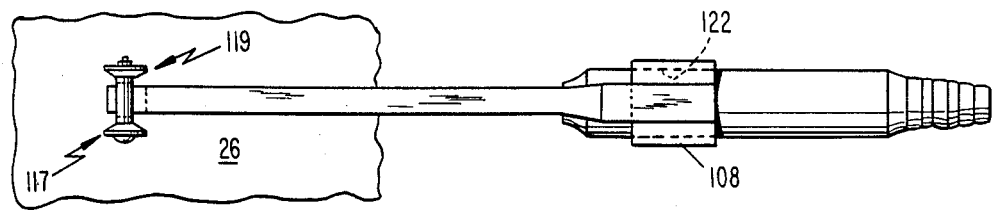
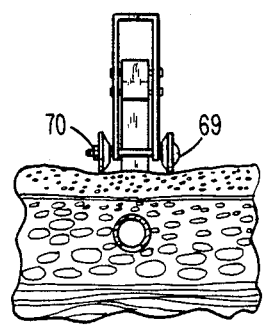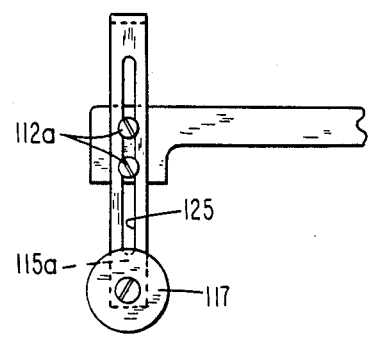
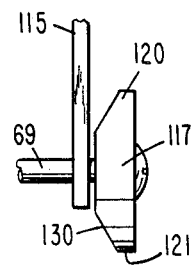

SURGICAL APPARATUS FOR PERFORMING SUCTION LIPECTOMY

RELATED APPLICATIONS

This application is a continuation-in-part of my P.C.T. International patent application, No. PCT/US85/00814 filed May 6, 1985 which PCT application is based on U.S. Ser. No. 607,714, filed May 17, 1984, and now U.S. Pat. No. 4,596,553, issued June 24, 1986; U.S. Ser. No. 651,720, filed Sept. 18, 1984; and U.S. Ser. No. 887,040, filed Jan. 3, 1986.

TECHNICAL FIELD

The present invention relates generally to surgical instruments and, more particularly, to a surgical cannula and its method of use in performing suction lipectomy to remove excessive accumulations of fatty tissue from a human body.

BACKGROUND ART

Suction lipectomy or lipolysis is a surgical procedure for removing fatty tissue and fatty tumors from localized areas of the human body through small incisions that can be easily concealed. The surgical procedure customarily employed requires an incision in the skin to expose the fatty tissue. The tip of a cannula is then inserted into the incision and manually directed by the surgeon towards the desired area of the body. By guiding the tip through the fatty tissue while simultaneously applying suction through a longitudinal passage extending through the cannula in communication with the tip, fat is surgically aspirated from the body. For adequate aspiration, approximately 15-20 strokes of the tip through the fatty tissue are often necessary.

FIG. 1 is an illustration of a conventional cannula 10 used for suction lipectomy having a tip 12 and a handle 14 formed at opposite ends thereof. Tip 10 has a hole 16 communicating with a central longitudinal passage 19 extending through the cannula for connection to a suction means 20 in a well known manner. To remove a desired amount of fat from fatty tissue 22 (see FIGS. 2 and 3), an incision 24 is first made in skin 26 to expose the tissue. Tip 10 is then inserted through incision 24 into tissue 26. By gripping handle 14 to move tip 12 through the fatty tissue in continuous reciprocating strokes (see arrows A and A') while applying suction, fat is surgically aspirated through hole 16 and passage 18. After a sufficient number of strokes by the surgeon, the original thickness T of fatty tissue is reduced to a lesser thickness T' (see FIG. 3A).

Because suction lipectomy is essentially cosmetic surgery, considerable surgical skill is necessary to repetitively guide tip 12 in directions A, A' to leave an even layer of tissue intact. This requires guiding tip 12 at a constant depth beneath the skin. Otherwise, different thicknesses of remaining tissue will cause permanent indentations 28 to appear in the skin following surgery (see FIG. 3A), which can be very unslightly. Unfortunately, however, the results frequently obtained with suction lipectomy are of the type shown in FIG. 3A, since the surgeon does not always know or cannot maintain the precise depth at which he guides tip 12 through the tissue. Further, since the surgeon must guide the tip in directions A,A', there is a tendency during the stroke to rotate (arrows B,B') the cannula about its longitudinal axis, causing hole 16 to move above or below the desired depth. Even if the surgeon possesses sufficient skill to guide tip 12 at constant depth, the large number of repetitive strokes necessary for adequate aspiration renders the surgical procedure fatiguing to the surgeon, possibly resulting in momentary loss of control while guiding the cannula.

To remove these permanent indentations 28 or wavy appearance in the skin frequency caused by use of conventional cannula 10, surgeons generally rely upon secondary surgery (i.e., suction lipectomy) to remove additional fatty tissue. Indeed, clinical observations reveal that secondary surgical procedures are employed on approximately 20-26% of patients initially undergoing suction lipectomy.

To avoid the foregoing problems and reduce the incidence of secondary surgery, my co-pending U.S. patent application, Ser. No. 651,720, filed Sept. 18, 1984, discloses a conventional cannula 10 including a parallel guide bar mounted thereon having a forward guide surface pressed by the surgeon into constant contact with the skin so that the suction hole remains at constant depth during reciprocation of the cannula through the fatty tissue. The guide bar, preferably formed of medical grade stainless steel, is connected at a rear end thereof to the cannula with a threaded bolt secured to the handle and a rear hinge fixing the guide bar to the handle. The guide bar includes a major elevated portion offset from forward and rear ends of the guide bar in a direction away from the cannula. By providing the elevated portion upon the guide bar, the surgeon is able to grip the elevated portion to facilitate reciprocating movement of the cannula through the fatty tissue and maintain the guide surface in contact with the skin when performing the surgical procedure on various parts and therefore different contours of the body (i.e., concave, convex or flat).

Friction between the guide surface and the skin surface tends to be minimized by providing a pair of wheels mounted to the guide bar tip with a cross bolt and nut. The wheels rotate freely on the bolt to provide tangential rolling contact with the skin surface for low friction movement during reciprocating strokes with the cannula.

Adjustment of the distance between the cannula and wheels is achieved by manipulation of nuts on the handle bolt to pivot the guide wheels towards or away from the cannula about the hinge. This bolt and hinge mechanism constitutes an improvement over the dual bolt mechanism disclosed in my prior co-pending patent application, Ser. No. 607,714, filed May 7, 1984, wherein spacing between the guide bar and cannula was achieved by adjustment of nuts provided upon both bolts.

In my prior invention described supra, it is necessary to modify the structure of the cannula handle to include a threaded hole accomodating the bolt and a post upon which the hinge is mounted. However, since conventional cannulas and handles thereof are not equipped with the above features, relatively expensive retro-fitting is required to machine and tap a threaded hole for receiving the bolt and to provide a mounting post for the hinge.

It is accordingly an object of the present invention to provide an improved guide bar structure connectible to a conventional cannula without requiring alteration of the cannula handle to mount the guide bar thereon.

Another object of the invention is to provide a guide bar that can be universally fitted to any type of cannula.

Still a further object is to provide a guide bar that is simple in design and economical to manufacture.

Still another object is to provide a guide bar structure which, when attached to a cannula, allows the cannula to be easily guided by the surgeon at constant depth so that a desired amount of fatty tissue is surgically aspirated while leaving an even thickness layer of tissue intact.

The wheels in my prior invention are generally parallel to each other and include peripheral surfaces in constant contact with the skin during reciprocation of the cannula by the surgeon. One of the problems with this arrangement is that the skin between the wheels and underlying cannula and soft fatty tissue immediately beneath the skin surface may sometimes bunch up beneath the wheels. This causes the wheels to become temporarily elevated in a localized area relative to the skin surface. This temporary elevation of the wheels causes a corresponding reduction in depth through which the cannula tip moves through fatty tissue possibly resulting in wavy indentations 28 to appear in the skin after the suction lipectomy procedure.

It is accordingly another object of the present invention to provide an improved guide wheel structure capable of stretching and stabilizing the skin between the wheels and underlying cannula to prevent localized changes of the elevation of the wheels relative to skin surface outwardly adjacent the wheels during reciprocating movement of the cannula.

Another object is to provide a guide bar having an adjustment mechanism for varying the distance between the cannula tip and guide wheels independent of the cannula handle.

DISCLOSURE OF THE INVENTION

A device for surgically aspirating subcutaneous fatty tissue from an animate body, in accordance with a first embodiment of the invention, comprises a cannula having a tip and a handle at opposite ends thereof. The tip is formed with a hole in communication with a longitudinal passage extending through the cannula. The passage is connectible to a source of vacuum so that suction can be applied to surgically aspirate fatty tissue through the hole when the tip is implanted in tissue. A guide bar is attached to the cannula for maintaining the hole at a predetermined desired depth within the tissue as the tip is manually directed by a surgeon. The guide bar is formed with an elevated portion between opposite ends thereof. In operation, only the guide surface is in sliding contact with the skin surface to control the depth of cannula tip; the elevated portion is gripped by the surgeon and allows the surgeon to manually contact the skin beneath the elevated portion to assist in manipulation of the cannula.

The guide bar preferably has a clamp at one end thereof connecting the guide bar to the cannula handle and an opposite free end terminating adjacent and spaced from the tip, with a guide surface facing the cannula. The clamp acts as a universal mount to facilitate secure attachment and rapid detachment of the guide bar to the cannula handle.

The guide surface is defined by a pair of wheels rotatably mounted to the free end of the guide bar to establish a low friction guide surface by virtue of rolling contact with the skin. During surgery, this guide surface contacts the skin surface overlying the fatty tissue to control the depth at which the tip removes fat so that an even thickness layer of tissue remains intact upon completion of surgery. Preferably, the peripheral guide surface of each wheel has an inner beveled edge coacting to stretch the skin between the wheels.

In accordance with a preferred embodiment of the invention, the rear end of the guide bar includes an annular sleeve into which the cannula handle is inserted and securely held in position by tightening screws passing through the sleeve. To vary the spacing between the guide wheels and cannula tip, the wheels are rotatably mounted to the lower end of height adjustment bar slidably mounted to the forward end of the guide bar by means of two vertically spaced screws passing through an elongate slot in the adjustment bar. By loosening the screws, the bar can travel vertically towards and away from the cannula tip to achieve the desired spacing; whereupon the screws are tightened to firmly press the adjustment bar to the forward end of the guide bar. Use of at least two vertically spaced screws within the elongate slot advantageously prevents the adjustment bar from pivoting out of vertical alignment during suction lipectomy as pressure is applied by the surgeon to the guide bar to firmly maintain the guide wheels in rolling contact with the skin during reciprocating movement of the cannula.

Still other objects of the present invention will become readily apparent to those skilled in this art from the following description wherein there is shown and described a preferred embodiment of this invention simply by way of illustration of one of the best modes contemplated for carrying out the invention. As will be realized, the invention is capable of other different embodiments, and its several details are capable of modifications in various, obvious respects, all without departing from the invention.

BRIEF DESCRIPTION OF THE DRAWING

FIG. 1 is a side elevational view of a conventional cannula commonly used to perform suction lipectomies;

FIG. 2 is a top view of an area of the body on which suction lipectomy is to be performed through an incision formed in the skin;

FIG. 3 is an enlarged fragmentary sectional view taken along the line 3—3 of FIG. 2 showing the tip of the prior art cannula of FIG. 1 inserted into the fatty tissue through the incision prior to surgical aspiration;

FIG. 3A is a view similar to FIG. 3 showing typical results obtained with the prior art cannula of FIG. 1 upon completion of the suction lipectomy;

FIG. 4 is a side elevational view of improvements, according to the present invention, to the guide bar and guide wheels thereon;

FIG. 4A is a sectional view taken along the line 4A—4A of FIG. 4;

FIG. 5 is a top plan view of the guide bar of FIG. 4;

FIG. 6 is a sectional view taken along the line 6—6 of FIG. 4;

FIG. 7 is a partial detailed view of improvements to the guide wheel assembly; and FIG. 8 is a partial sectional view of improvements to the guide wheels.

BEST MODE FOR CARRYING OUT THE INVENTION

Guide bar 100 according to the present invention includes forward and rear opposite ends 102 and 104, respectively, and an elevated portion elevated away from the cannula body by being offset from the forward and rear ends in a direction away from the cannula. As depicted in FIG. 4, the rear end 104 is formed with an annular mounting sleeve 108 through which handle 14 of a conventional cannula 10 is inserted and firmly retained by means of tightening screws 110. Forward end 102 supports, via clamping screws 112, a vertical height adjustment bar 115 rotatably supporting, at a lower end 115a thereof, a pair of guide wheels 117,119 having identical peripheral guide surfaces 120 thereon adapted to make rolling contact with skin 26 during reciprocating movement of cannula 10 so that the cannula hole is embedded in tissue 22 at a predetermined desired depth C.

Sleeve 108, preferably of medical grade stainless steel, is welded or otherwise fixed to the lower surface of rear end 104 and includes a passage 122 of sufficient diameter to receive handle 14 inserted into the sleeve. A pair of threaded holes 124 formed in the lower surface of sleeve 108 are adapted to receive a pair of longitudinally spaced tightening screws extending radially into the passage. These tightening screws bear against cannula handle 14 to clamp same into tight fitting contact with the sleeve to prevent axial movement during the suction lipectomy procedure.

By forming guard 100 with mounting sleeve 108, it will be appreciated that the guard is capable of use with virtually any type of commercially available cannula by simply inserting the cannula handle into the sleeve and thereafter tightening screws 110 to clamp the handle to the guide bar. While the passage 122 is disclosed as being of circular cross-section, it will be appreciated that sleeve 108 can be manufactured to have an internal cross-section compatible with the cross-section of a cannula handle that may be commercially available. In addition, sleeve 108 may be modified in light of the teachings herein so long as it performs the clamping function. For example, sleeve 108 may be manufactured as a split sleeve having interior clamping surfaces bearing against the cannula handle upon tightening the two halves of the sleeve towards each other and against the handle using screw means.

Height adjustment bar 115, preferably also of medical grade stainless steel, is mounted to forward end 102 of guide bar 100 by means of vertically spaced screws 112 passing through elongate slot 125 formed in upper portions of the adjustment bar. Screws 112 include screw heads 112a preferably of larger diameter than the width of slot 125 so that the screw heads serve to clamp the adjustment bar to the guide bar upon tightening of the screws. The lower end 115a carries guide wheels 117,119 rotatably mounted in laterally spaced relationship to each other upon a cross bolt 69 carrying nut 70. Wheels 117,119 rotate freely on bolt 69 (unthreaded along an intermediate portion thereof) to provide tangential rolling contact with the skin surface for low friction movement during reciprocating strokes of the cannula.

With reference to FIG. 8, each wheel 117,119 preferably includes, on the peripheral surface 120 thereof, an inner beveled edge 130 inclined outwardly and downwardly towards a narrow annular surface 121 of the peripheral edge. The beveled edge 130 assists in stabilizing the skin between the wheels during the suction lipectomy procedure by stretching the skin so that the cannula tip moves at constant depth through fatty tissue 20.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A device for positioning a tip of a cannula at a generally constant depth within subcutaneous fatty tissue to surgically aspirate the tissue upon application of suction supplied thereto through the tip, comprising guide bar means mounted on the cannula for maintaining said tip at said generally constant depth as said tip is manually directed by a surgeon through the tissue in reciprocating strokes, said guide bar means including at one end thereof means for clamping the guide means to a handle of the cannula, said guide means including at an opposite end thereof a vertically movable height adjustment means rotatably mounted to the guide bar means which includes a rolling guide surface adapted to contact a portion of the skin covering the fatty tissue to locate and maintain the cannula tip at a generally constant depth as said tip is manually directed by a surgeon through the tissue in reciprocating strokes causing corresponding rolling movement of the guide surface on the skin, said height adjustment means including means for tightening it to the guide bar means to fix the rolling guide surface in a selected spaced location to the tip.

2. The device of claim 1, wherein said height adjustment means includes a height adjustment bar fixed to said opposite end of the guide bar, a lower end of the adjustment bar supporting said guide surface.

3. The device of claim 2, wherein the lower end of the height adjustment bar includes a pair of guide wheels rotatably mounted thereon, a peripheral surface of said guide wheels defining said guide surface.

4. The device of claim 3, wherein said height adjustment bar includes an elongate slot formed upwardly from the guide wheels, and a pair of vertically spaced screws connecting the height adjustment bar to the forward end of the guide bar through said slot.

5. The device of claim 4, wherein each guide wheel is formed with an inner beveled edge intersecting the peripheral surface of the associated guide wheel.

6. The device of claim 1, wherein said clamping means is a sleeve secured to said one end of the guide bar means and means for tightening the sleeve to urge the cannula handle into tight contact with the sleeve.

7. The device of claim 6, wherein said tightening means includes at least one tightening screw extending radially through the sleeve into contact with the cannula handle.

8. The device of claim 7, wherein said sleeve includes an inner cylindrical surface against which the cannula handle is clamped.

9. The device of claim 6, wherein said height adjustment means includes a height adjustment bar fixed to said opposite end of the guide bar, a lower end of the adjustment bar supporting said guide surface.

10. Apparatus for performing suction lipectomy comprising in combination a cannula having a handle and tip at opposite ends thereof and a passage through which suction is applied to the tip, said tip being positionable at a constant depth within subcutaneous fatty tissue to surgically aspirate the tissue upon application of suction supplied thereto through the tip; and guide means mounted on the cannula for maintaining said tip at said constant depth as said tip is manually directed by a surgeon through the tissue in reciprocating strokes, said guide means including at one end thereof a guide wheel means rotatably mounted thereto and having a peripheral surface defining a rolling guide surface adapted to contact a portion of the skin covering the fatty tissue to locate and maintain the cannula tip at a substantially constant depth as said cannula is manually directed by a surgeon through the tissue in reciprocating strokes causing corresponding movement of the guide surface on the skin, and further including a height adjustment bar fixed to said end of the guide bar, a lower end of the adjustment bar supporting said guide wheel means, and means for moving said height adjustment bar and whereby said guide wheel means towards or away from the cannula tip in a direction generally perpendicular to the longitudinal axis of the cannula to thereby vary the spacing between said guide wheel means and cannula tip.

11. The apparatus of claim 10, wherein the lower end of the adjustment bar includes a pair of guide wheels rotatably mounted thereon, a peripheral surface of said guide wheels defining said guide surface.

12. The apparatus of claim 11, wherein said height adjustment bar includes an elongate slot formed upwardly from the guide wheels, and a pair of vertically spaced screws connecting the height adjustment bar to the forward end of the guide bar through said slot.

13. The apparatus of claim 11, wherein each guide wheel is formed with an inner beveled edge intersecting the peripheral surface of the associated guide wheel.

* * * * *